United States Patent
Yoon (10) Patent No.: US 11,484,332 B2
(45) Date of Patent: Nov. 1, 2022

(54) ENDOSCOPIC TREATMENT TOOL

(71) Applicant: CATHOLIC KWANDONG UNIVERSITY INDUSTRY COOPERATION FOUNDATION, Gangneung-si (KR)

(72) Inventor: Cheesoon Yoon, Seoul (KR)

(73) Assignee: CATHOLIC KWANDONG UNIVERSITY INDUSTRY COOPERATION FOUNDATION, Gangneung-si (KR)

( * ) Notice: Subject to any disclaimer, the term of this patent is extended or adjusted under 35 U.S.C. 154(b) by 81 days.

(21) Appl. No.: 16/472,697

(22) PCT Filed: Dec. 14, 2017

(86) PCT No.: PCT/KR2017/014674
§ 371 (c)(1),
(2) Date: Jun. 21, 2019

(87) PCT Pub. No.: WO2018/124555
PCT Pub. Date: Jul. 5, 2018

(65) Prior Publication Data
US 2019/0365403 A1 Dec. 5, 2019

(30) Foreign Application Priority Data
Dec. 26, 2016 (KR) .................. 10-2016-0178890

(51) Int. Cl.
*A61B 17/29* (2006.01)
*A61B 1/00* (2006.01)
*A61B 17/00* (2006.01)

(52) U.S. Cl.
CPC ...... *A61B 17/2909* (2013.01); *A61B 1/00144* (2013.01); *A61B 2017/0046* (2013.01);
(Continued)

(58) Field of Classification Search
CPC ..... A61B 10/06; A61B 17/2909; A61B 1/018; A61B 2017/0046; A61B 2017/00473;
(Continued)

(56) References Cited

U.S. PATENT DOCUMENTS 5,466,222 A * 11/1995 Ressemann ......... A61M 25/104
604/103.09
6,059,719 A 5/2000 Yamamoto
(Continued)

FOREIGN PATENT DOCUMENTS

JP 08-182678 A 7/1996
JP 11-047079 A 2/1999
(Continued)

OTHER PUBLICATIONS

International Search Report for PCT/KR2017/014674, dated Mar. 23, 2018.

*Primary Examiner* — Brooke Nicole Labranche
(74) *Attorney, Agent, or Firm* — Sughrue Mion, PLLC (57) ABSTRACT

The present invention relates to an endoscopic treatment instrument, and more particularly, to an endoscopic treatment instrument including a detachable end-effector and a contamination prevention cover. The endoscopic treatment instrument includes an end-effector for performing treatment in the endoscopic surgery or an endoscope treatment, a connection section being detachably coupled to an end of the end-effector, and a contamination prevention cover being coupled to the connection section or the end-effector and surrounding a portion of an outer peripheral surface of the connection section so as to prevent contamination of the connection section. According to an embodiment of the present invention, since only the end-effector is separable for replacement and the cover is formed to protect a control unit, it is possible to prevent cross infection between patients caused by the contamination of the end-effector and the control unit.

8 Claims, 4 Drawing Sheets

(52) U.S. Cl.
CPC ............... *A61B 2017/00477* (2013.01); *A61B 2017/2902* (2013.01); *A61B 2017/2905* (2013.01); *A61B 2217/007* (2013.01)

(58) Field of Classification Search
CPC .. A61B 2017/00477; A61B 2017/2901; A61B 2017/2902; A61B 2017/2905; A61B 2017/2931; A61B 2017/2939; A61B 2017/294; A61B 2217/007; A61B 46/01; A61B 90/40
See application file for complete search history.

(56) References Cited

U.S. PATENT DOCUMENTS

| | | | | |
|---|---|---|---|---|
| 2006/0258905 | A1* | 11/2006 | Kaji | A61B 1/018 600/106 |
| 2008/0243106 | A1* | 10/2008 | Coe | A61B 17/00 606/1 |
| 2016/0045099 | A1* | 2/2016 | Farhadi | A61B 1/00142 600/116 |

FOREIGN PATENT DOCUMENTS

| | | |
|---|---|---|
| JP | 2002-159436 A | 6/2002 |
| JP | 2005-211205 A | 8/2005 |
| JP | 2016-193002 A | 11/2016 |
| KR | 10-2015-0128222 A | 11/2015 |

\* cited by examiner

ENDOSCOPIC TREATMENT TOOL

CROSS REFERENCE TO RELATED APPLICATIONS

This Application is a National Stage of International Application No. PCT/KR2017/014674 filed Dec. 14, 2017, claiming priority based on Korean Patent Application No. 10-2016-0178890 filed Dec. 26, 2016.

TECHNICAL FIELD

The present invention relates to an endoscopic treatment instrument, and more particularly, to an endoscopic treatment instrument having a detachable end-effector.

BACKGROUND ART

An endoscope is a medical instrument that allows direct observation of internal organs or body cavities. The endoscope is used to observe internal organs or body cavities as well as to facilitate resection of tissues and collection of secretions, so that it is very helpful in the detection and diagnosis of diseases and the treatment thereof.

In order to diagnose or treat diseases using an endoscope, a treatment instrument with end-effectors, such as electrocauteries, forceps, and cutters, is inserted into the human body together with the endoscope, in which state the affected part is observed with the endoscope and the procedure is performed with the treatment instrument.

Since the treatment instrument is contaminated with various internal secretions, such as saliva or blood of an examinee and germs after the procedure is performed, it is necessary to remove contaminants from the treatment instrument by washing and disinfection before it is reused for the next examinee. However, the examinees are always exposed to the risk of infection because the treatment instrument is insufficiently disinfected.

In order to minimize the risk of infection, it is desirable to use a new treatment instrument for each examinee, which is practically impossible due to the high unit price of treatment instrument parts including a control unit for controlling an end-effector, and the like.

Therefore, there has been a demand for an endoscopic treatment instrument, the remaining part of which is usable as it is while separating only an end-effector therefrom for replacement.

SUMMARY OF INVENTION

Technical Problem

It is an object of the present invention to provide an endoscopic treatment instrument that can replace only an end-effector for use by separating the end-effector from a control unit for controlling the end-effector, namely, from a part behind the end-effector including an articulated manipulator, a hard shaft with no joint, or a bendable sheath.

The present invention is not limited to the above-mentioned object, and other objects of the present invention can be clearly understood by those skilled in the art to which the present invention pertains from the following description.

Solution to Problem

In accordance with an aspect of the present invention, there is provided an endoscopic treatment instrument that includes an end-effector for performing treatment in the endoscopic treatment instrument or an endoscope surgical instrument, a connection section being detachably coupled to an end of the end-effector, and a contamination prevention cover being coupled to the connection section or the end-effector and surrounding a portion of an outer peripheral surface of the connection section to prevent contamination of the connection section.

In the present invention, the end-effector may have a coupling groove being recessed inward from the end thereof. The connection section may include a joint part being detachable from the coupling groove and being bendable, a transmission part being connected to the joint part, and a control unit for controlling bending of the joint part by using the transmission part. A position of the end-effector may be controlled by the joint part.

In the present invention, an inner peripheral surface of a region of the contamination prevention cover may be formed so as to cover an outer peripheral surface of a region of the end-effector.

In the present invention, the endoscopic treatment instrument may further include a handle part being connected to a portion of the end-effector so as to control an operation of the end-effector outside the end-effector.

In the present invention, the contamination prevention cover may be made of a flexible material so as to be easily folded and unfolded.

In the present invention, the end-effector and the connection section may be coupled to each other in a screwing manner or a concave-convex manner.

In the present invention, the endoscopic treatment instrument may further include a contamination prevention cover mounting unit being coupled to an end of the contamination prevention cover. The contamination prevention cover mounting unit may include a main body having a first through-hole formed longitudinally therein so that the connection section may be inserted, and a fluid injection part having a second through-hole formed through the main body so as to communicate with the first through-hole.

In the present invention, the contamination prevention cover may be expanded when a fluid is injected thereinto.

In the present invention, the endoscopic treatment instrument may further include a plurality of bands arranged longitudinally on the contamination prevention cover, and the plurality of bands may be inserted into the contamination prevention cover or attached to an outer peripheral surface of the contamination prevention cover so as to suppress longitudinal expansion of the contamination prevention cover.

Advantageous Effects of Invention

In accordance with exemplary embodiments of the present invention, since only an end-effector is separable for replacement and a cover is formed to protect other parts, it is possible to prevent cross infection between patients caused by the contamination of an endoscopic treatment instrument.

The present invention is not limited to the above effect, and it should be understood that the present invention includes all effects which can be inferred from the following detailed description of the present invention or the configuration of the invention defined by the appended claims.

DESCRIPTION OF EMBODIMENTS

Reference will now be made in detail to exemplary embodiments of the present invention, examples of which are illustrated in the accompanying drawings. The present invention may, however, be embodied in different forms and should not be construed as limited to the embodiments set forth herein. For clear explanation of the present invention, parts irrelevant to the description may be omitted in the drawings, and like reference numerals refer to like parts throughout the specification.

In the whole specification, it will be understood that when an element is referred to as being "connected (joined, contacted, or coupled)" to another element, it can be "directly connected" to the other element or it can be "indirectly connected" to the other element with other elements being interposed therebetween. In addition, it will be understood that when a component is referred to as "comprising or including" any component, it does not exclude other components, but can further comprise or include the other components unless otherwise specified.

The terminology used herein is for the purpose of describing particular embodiments only and is not intended to limit the invention. As used in the disclosure and the appended claims, the singular forms "a", "an" and "the" are intended to include the plural forms as well, unless context clearly indicates otherwise. It will be further understood that the terms "comprises/includes" and/or "comprising/including" when used in this specification, specify the presence of stated features, integers, steps, operations, elements, components, and/or groups thereof, but do not preclude the presence or addition of one or more other features, integers, steps, operations, elements, components, and/or groups thereof.

Hereinafter, exemplary embodiments of the present invention will be described in detail with reference to the accompanying drawings.

Figure 1:
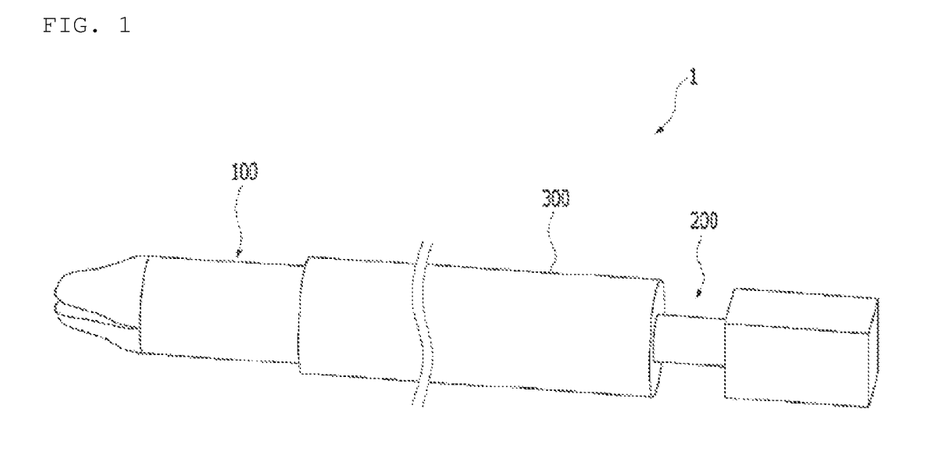
FIG. 1 is a perspective view illustrating an endoscopic treatment instrument according to an embodiment of the present invention.

FIG. 1 is a perspective view illustrating an endoscopic treatment instrument 1 according to an embodiment of the present invention. The endoscopic treatment instrument 1 is an instrument that is inserted into a body cavity through a working channel of an endoscope and performs tests or treatment, and includes an end-effector 100, a connection section 200, and a contamination prevention cover 300.

The end-effector 100 is a component that is inserted into the body cavity and performs treatment. Although the end-effector 100 is illustrated as forceps in FIG. 1, the present invention is not limited thereto. Of course, the end-effector 100 may be formed in various forms such as an electrocautery and a cutter.

The connection section 200 is detachable from the end-effector 100, and may be an articulated manipulator, a hard shaft with no joint, or a bendable sheath. For example, in the case where the connection section 200 is a manipulator, a portion of the connection section 200 may be bent freely in all directions so as to adjust the position of the end-effector 100. In an embodiment of the present invention, a communication line may be formed in the connection section 200 and the end-effector 100, and the communication line enables the connection section 200 to control the position and operation of the end-effector 100.

The contamination prevention cover 300 is a component that surrounds an outer peripheral surface of the connection section 200 and prevents contamination of the outer peripheral surface of the connection section 200 with bloods, in-body secretions, etc., and is coupled to a region of the outer peripheral surface of the end-effector 100. When the contamination prevention cover 300 is completely separated from or coupled to the end-effector 100, it may be coupled to the end or a portion of the connection section 200.

The contamination prevention cover 300 is preferably made of a material having elasticity, including at least one selected from the group consisting of polyester, spandex, latex, and silicone, so that it is pressed against the outer peripheral surface of the connection section 200, but the present invention is not limited thereto.

Preferably, the contamination prevention cover 300 has a thickness of 0.005 mm to 0.5 mm. If the thickness is less than 0.005 mm, it may be torn during insertion into the body, and if the thickness is more than 0.5 mm, it may not be inserted into the working channel due to an increase in diameter.

Figure 2:
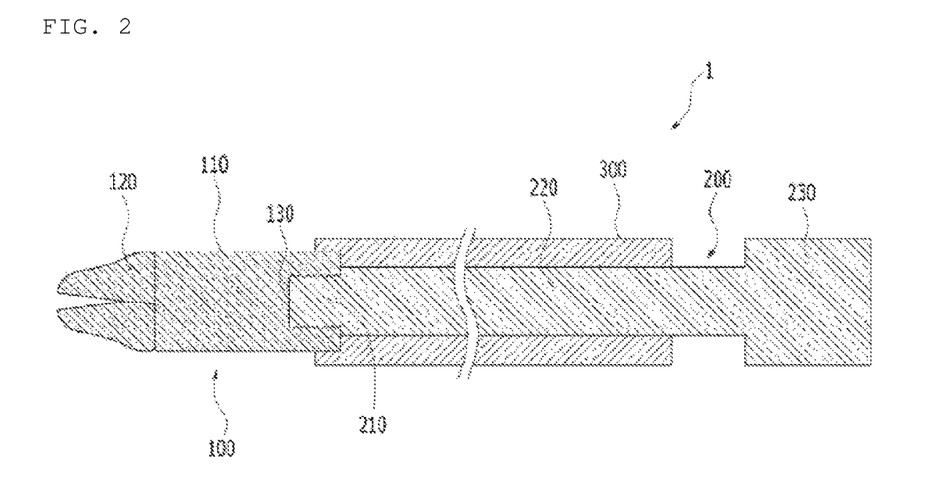
FIG. 2 is a cross-sectional view illustrating the endoscopic treatment instrument according to the embodiment of the present invention.
Figure 3:
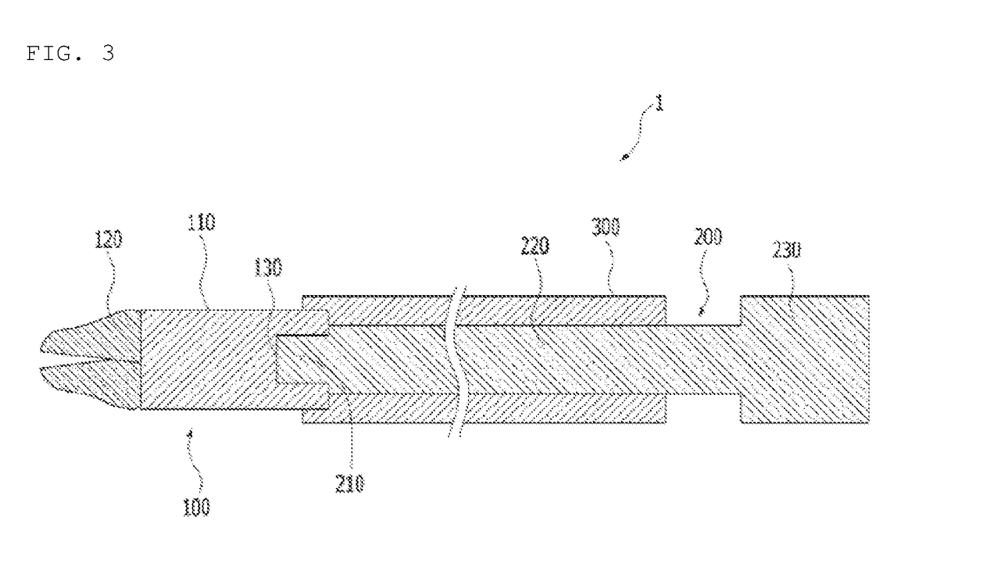
FIG. 3 is a cross-sectional view illustrating the endoscopic treatment instrument according to the embodiment of the present invention.

FIGS. 2 and 3 are cross-sectional views illustrating the endoscopic treatment instrument 1 according to the embodiment of the present invention.

Referring to FIGS. 2 and 3, the end-effector 100 includes a coupling part 110 and an operation part 120.

The coupling part 110 is a component that couples the operation part 120 to the connection section 200. The coupling part 110 may have a coupling groove 130 being formed in the end thereof in order to prevent the separation of the coupling part 110 from the connection section 200. When the coupling groove 130 is formed, the connection section 200 has a protrusion-shaped joint part 210 being formed at an end thereof so as to correspond to the coupling groove 130. The joint part 210 will be described in detail below.

In an embodiment of the present invention, the coupling groove 130 may have a first thread formed at an inner peripheral surface thereof, and the joint part 210 may have a second thread formed at an outer peripheral surface thereof so as to correspond to the first thread, with the consequence that the connection section 200 and the end-effector 100 can be screwed to each other. According to an embodiment of the present invention, when the connection section 200 controls not only the position of the end-effector 100 but also the operation of the operation part 120, the coupling groove 130 may be formed with a communication line in order to transmit an operation signal generated in the connection section 200 to the coupling part 110, and the joint part 210 of the connection section 200 may be formed with a communication line in order to transmit a signal for controlling the operation of the coupling part 110. When the joint part 210 and the coupling groove 130 are coupled to each other, two communication lines may be interconnected such that the operation of the operation part 120 can be controlled.

The connection section 200 includes a transmission part 220, a joint part 210, being connected to one end of the transmission part 220, being bendable in all directions, and being detachable from the end-effector 100, and a control unit 230 which is connected to the other end of the transmission part 220 and controls the bending of the joint part 210. That is, the bending of the joint part 210 is controlled by the control unit 230 so that the joint part 210 may change the position of the end-effector 100. In this case, the joint part 210 is bendable in all directions by continuously coupling a plurality of ring-shaped rings thereto.

The contamination prevention cover 300 is coupled such that a region of the inner peripheral surface thereof abuts on a region of the outer peripheral surface of the coupling part 110. In an embodiment of the present invention, the contamination prevention cover 300 and the end-effector 100 are integrally formed so that the end-effector 100 and the contamination prevention cover 300 can be replaced at one time after endoscopy is completed.

Figure 4:
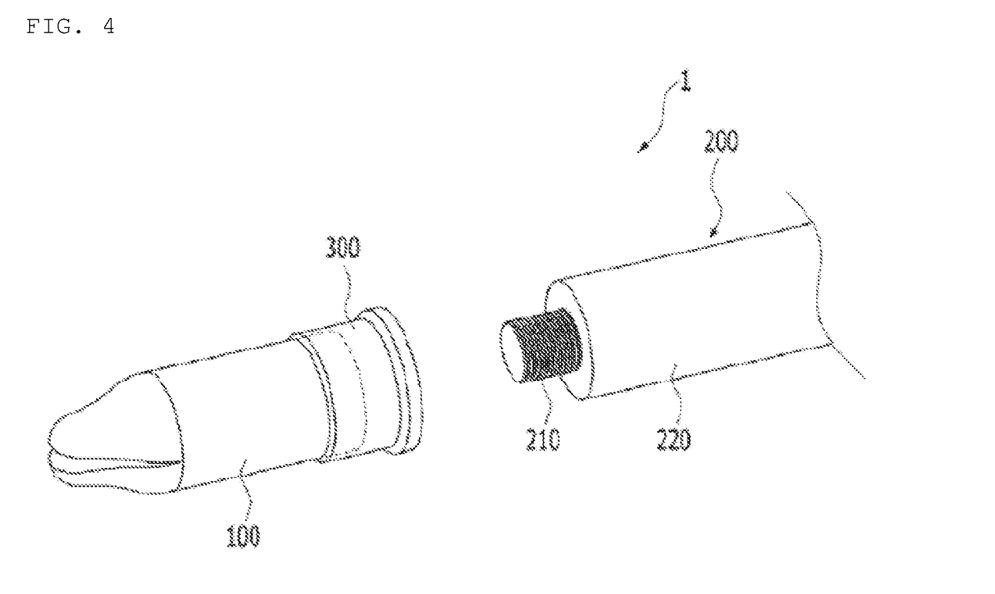
FIG. 4 is an enlarged view illustrating the endoscopic treatment instrument according to the embodiment of the present invention.

FIG. 4 is an enlarged view illustrating the endoscopic treatment instrument 1 according to the embodiment of the present invention. FIG. 4 illustrates a state before the end-effector 100 and the connection section 200 are coupled to each other. In this case, the contamination prevention cover 300 being coupled to an end of the end-effector 100 is rolled up (or folded), with the consequence that the contamination prevention cover 300 may not interrupt the coupling between the end-effector 100 and the connection section 200 compared to when it is unfolded. After coupling, the contamination prevention cover 300 is unfolded by the user to cover the outer peripheral surface of the connection section 200, thereby preventing the contamination of the connection section 200.

Figure 5A:
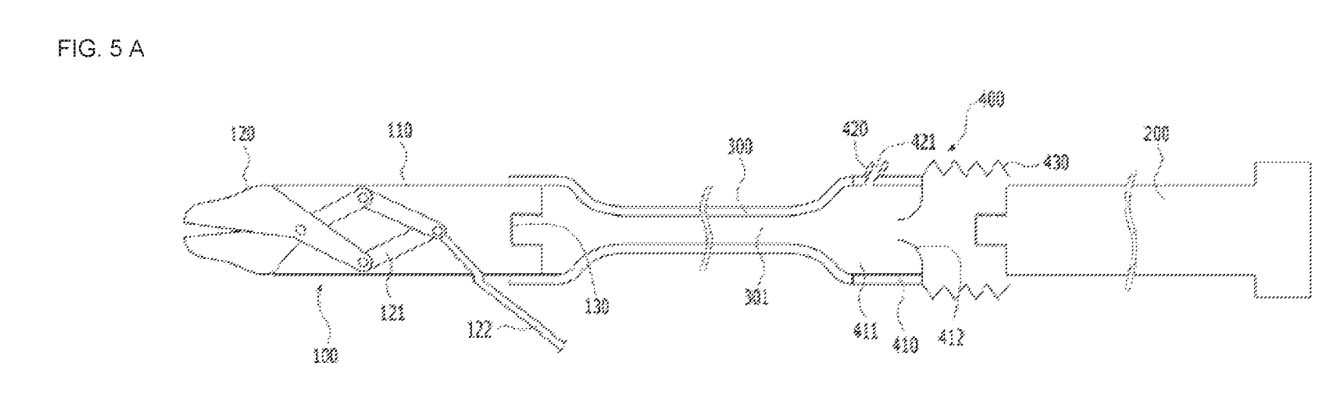
FIGS. 5A and 5B are enlarged cross-sectional views illustrating the endoscopic treatment instrument according to the embodiment of the present invention.
Figure 5B:
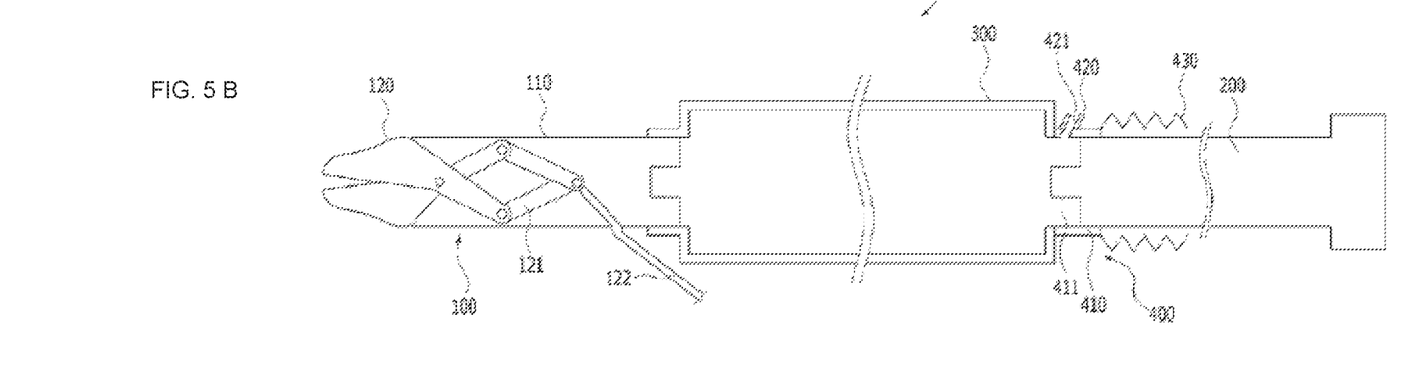

FIGS. 5A and 5B are enlarged cross-sectional views illustrating the endoscopic treatment instrument 1 according to the embodiment of the present invention. FIG. 5A illustrates a state before the connection section 200 is inserted into a contamination prevention cover mounting unit 400.

In an embodiment of the present invention, the end-effector 100 includes a coupling part 110, an operation part 120, an operation module 121, and a handle part 122. Since the coupling part 110 and the operation part 120 are the same as those described above, a description thereof will be omitted.

The operation module 121 is a component that mechanically operates the operation part 120. The operation module 121 is connected to an end of the operation part 120, and is located inside the coupling part 110. The operation module 121 operates the operation part 120 according to the movement thereof.

The handle part 122 is a component that moves the operation module 121, and is connected to one end of the operation module 121. Although it is preferable that the handle part 122 protrudes outward through the coupling part 110 so that the user can operate the handle part 122, the present invention is not limited thereto. When the user pulls the handle part 122, the operation module 121 connected to the handle part 122 may move so as to operate the operation part 120 being connected to an end of the operation module 121.

According to an embodiment of the present invention, the contamination prevention cover mounting unit 400 may be formed at an end of the contamination prevention cover 300. The contamination prevention cover mounting unit 400 is a component that is coupled to the contamination prevention cover 300 and expands or contracts the contamination prevention cover 300, and includes a main body 410 and a fluid injection part 420.

The main body 410 has a first through-hole 411 being formed longitudinally therein, and communicates with a through-hole 301 of the contamination prevention cover 300.

The fluid injection part 420 protrudes from the outer peripheral surface of the main body 410, and has a second through-hole 421 being communicated with the first through-hole 411. In this case, a fluid injector (not shown) may be fitted into the second through-hole 421.

In an embodiment of the present invention, a packing 412 may be coupled to the inner peripheral surface of the main body 410 along the inner periphery thereof. The packing 412, when the connection section 200 is inserted into the contamination prevention cover mounting unit 400, seals between the contamination prevention cover mounting unit 400 and the connection section 200, thereby preventing the fluid in the contamination prevention cover 300 from leaking.

In an embodiment of the present invention, a control unit cover 430 may be coupled to an end of the main body 410 along the outer periphery at the outer peripheral surface thereof. The control unit cover 430 is a component that prevents the contamination of the control unit 230 that is not inserted into the contamination prevention cover 300. FIG. 5A illustrates a state in which the control unit cover 430 is folded in the process of inserting or withdrawing the connection section 200 into or from the contamination prevention cover 300, in which case the unfolded control unit cover 430 does not interrupt the insertion or withdrawal process of the connection section 200. When the insertion of the connection section 200 is completed, the user can unfold the control unit cover 430 in order to prevent the contamination of the control unit 230. Although the control unit cover 430 is preferably made of a flexible material such as rubber or synthetic resin so that it is easily folded and unfolded, but the present invention is not limited thereto.

FIG. 5B illustrates a state in which the contamination prevention cover 300 is expanded. This illustrates that after the connection section 200 is partially inserted into the contamination prevention cover mounting unit 400 in the state of FIG. 5A so that the connection section 200 and the contamination prevention cover mounting unit 400 are completely sealed by the packing 412, a fluid is injected through the fluid injection part 420 and the contamination prevention cover 300 is expanded. In this case, the fluid passes through the second through-hole 421 and flows from the first through-hole 411 to the contamination prevention cover 300, thereby expanding the contamination prevention cover 300. The expanded contamination prevention cover 300 facilitates the insertion of the connection section 200, rather than the unexpanded contamination prevention cover 300.

Meanwhile, the fluid is injectable even though the contamination prevention cover mounting unit 400 does not have the second through-hole, in which case the fluid can also be injected along with the insertion of the connection section 200 into the first through-hole.

A plurality of bands (not shown) may be longitudinally attached to the outer peripheral surface of the contamination prevention cover 300. The plurality of bands suppress the longitudinal expansion of the cover 300, thereby facilitating the insertion of the endoscope. In this case, the plurality of bands may be attached to the outer peripheral surface of the cover 300, and may be inserted between a cover 300 and another cover 300 when these covers 300 are manufactured.

Preferably, the plurality of bands are radially arranged with respect to the center of the cover 300 to prevent the longitudinal expansion occurring in only a specific portion. Each of the plurality of bands may be made of a rubber material or synthetic resin having an expansion coefficient lower than the cover 300, or may be formed of a polymer material having less longitudinal elasticity at the same time when the cover 300 is manufactured.

Figure 6:
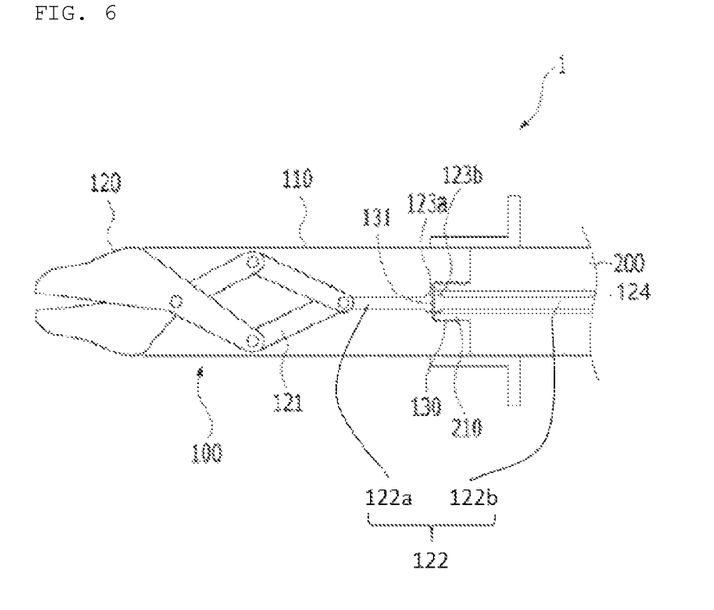
FIG. 6 is an enlarged cross-sectional view illustrating the endoscopic treatment instrument according to an embodiment of the present invention.

FIG. 6 is an enlarged cross-sectional view illustrating an endoscopic treatment instrument 1 according to an embodiment of the present invention. The same components as those in FIGS. 4 and 5 are designated by the same reference numerals, and a description thereof will be omitted.

Unlike in FIGS. 5A and 5B, FIG. 6 illustrates that there are provided two handle parts 122a and 122b passing through the coupling part 110 and the connection section 200, respectively, and the handle part 122b protrudes to the outside. In this case, the connection section 200 is formed with a through-hole 124 through which the handle part 122b passes. In addition, a membrane 131 is formed between the two handle parts 122a and 122b. The membrane 131 is preferably made of an elastic material such as rubber so as to be movable together with the handle parts 122a and 122b according to the movement of the handle parts 122a and 122b. The two handle parts 122a and 122b have attachment portions 123a and 123b formed at respective one ends thereof. The attachment portions 123a and 123b are attached to the membrane 131 or are made of an attractive material such as a magnet so as not to be detached from the membrane 131.

When the handle parts 122a and 122b protrude outward through the coupling part 110 and the connection section 200, the handle parts 122a and 122b and the control unit 300 are easily operated with one hand, thereby improving a user's operational convenience. In addition, since the two handle parts 122a and 122b move in a state in which they are separated from each other by the membrane 131, it is possible to prevent the control unit 300 from being contaminated by the handle parts 122a and 122b.

When the endoscopic treatment instrument 1 according to the embodiment of the present invention is used, only the end-effector 100 can be separated and replaced. In addition, since the connection section 200 is protected by the contamination prevention cover 300, it is possible to prevent infection between patients caused by the contamination of the end-effector 100 and the connection section 200.

Figure 7:
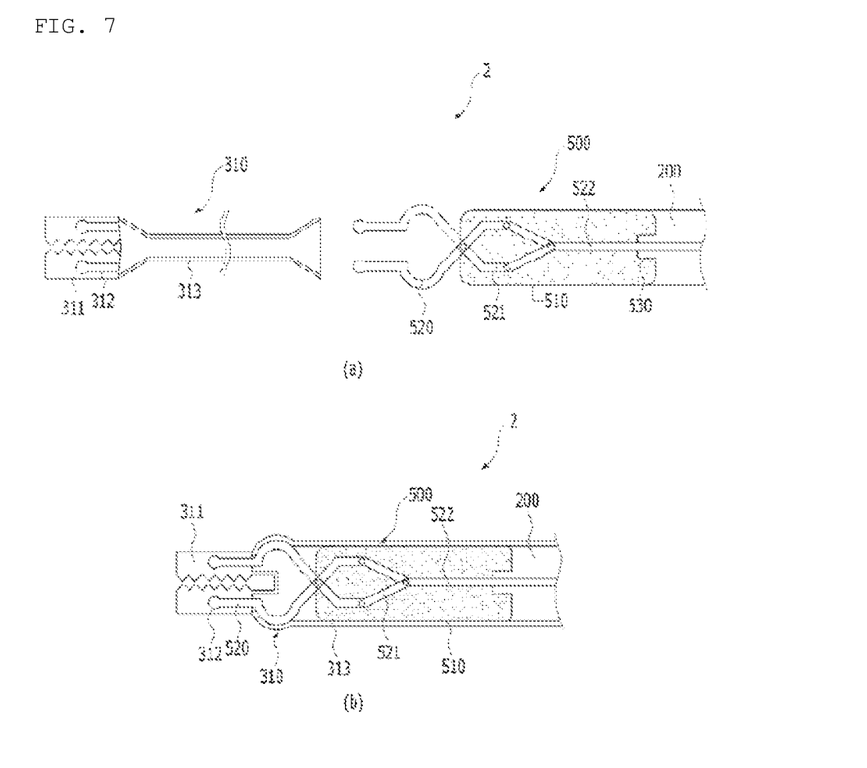
FIGS. 7A and 7B are reference views illustrating a process of using an endoscopic treatment instrument including a treatment instrument cover according to an embodiment of the present invention.

FIGS. 7A and 7B are reference views illustrating a process of using an endoscopic treatment instrument 2 including a treatment instrument cover 310 according to an embodiment of the present invention.

The endoscopic treatment instrument 2 includes a connection section 200, an end-effector 500, and a treatment instrument cover 310.

The end-effector 500 according to the embodiment of FIGS. 7A and 7B includes a coupling part 510 and an operation part 520. The coupling part 510 has a coupling groove 530 being formed in an end thereof in order to couple the connection section 200 and the coupling part 510, and the operation part 520 is connected to the other end of the coupling part 510. The coupling part 510 has an operation module 521 formed therein so that the operation module 521 is connected to the operation part 520 to operate the operation part 520.

A handle part 522 is connected to an end of the operation module 521 to move according to the movement of the handle part 522, thereby operating the operation part 520.

The treatment instrument cover 310 is a component that prevents the contamination of the end-effector 500 and the connection section 200. The treatment instrument cover 310 is formed therein with a groove 312 into which the operation part 520 is fitted. The treatment instrument cover 310 includes an operation part cover 311 moving according to the movement of the operation part 520, and a connection section cover 313, which is coupled along the outer peripheral surface at the outer periphery of the operation part cover 311 and surrounds the outer peripheral surfaces of the coupling part 510 and the connection section 200. In this case, the treatment instrument cover 310 may be changed into various treatment instruments according to the shape, and FIGS. 7A and 7B illustrates a cutter-shaped treatment instrument cover 310.

FIG. 7B is a view illustrating a state in which the end-effector 500 is inserted into the operation part cover 311 and the connection section cover 313. The operation part cover 520 of the end-effector 500 is partially inserted into the groove 312 of the operation part cover 311, and the operation part 520 which are not inserted into the operation part cover 311, the coupling part 510, and the connection section 200 are inserted into the connection section cover 313.

One or more bands (not shown) may be longitudinally arranged at the outer peripheral surface of the contamination prevention cover 300. The bands suppress the longitudinal expansion of the contamination prevention cover 300, thereby facilitating the insertion of the connection section. In this case, the bands may be attached to the outer peripheral surface of the contamination prevention cover 300, and may be inserted between a contamination prevention cover 300 and another contamination prevention cover 300 when these covers 300 are manufactured. Preferably, the bands are radially arranged with respect to the center of the contamination prevention cover 300 to prevent the longitudinal expansion occurring in only a specific portion. Each of the bands may be made of a rubber material or synthetic resin having an expansion coefficient lower than the contamination prevention cover 300, or may be formed of a polymer material having less longitudinal elasticity. That is, the contamination prevention cover 300 and the band have different expansion coefficients.

When the endoscopic treatment instrument 2 according to the embodiment of the present invention is used, it is possible to prevent the contamination of the operation part 520 and the connection section 200, which are relatively expensive, and to reuse them. In addition, since the treatment instrument can be changed into various treatment instruments according to the shape of the treatment instrument cover 310, it is possible to improve economic efficiency and simultaneously to prevent cross infection between patients.

The above-mentioned embodiments of the present invention are merely examples, and it will be understood by those skilled in the art that various modifications may be made without departing from the spirit and scope or essential features of the invention. Therefore, it should be understood that the embodiments described above are for purposes of illustration only in all aspects and are not intended to limit the scope of the present invention. For example, each component described in a single form may be implemented in a distributed form, and similarly, components described in the distributed form may be implemented in a combined form.

The scope of the present invention is defined by the appended claims, and it should be construed that all modifications or variations derived from the meaning, scope, and equivalent concept of the claims fall within the scope of the invention.

EMBODIMENTS

The embodiments of the present invention have been described together in the best mode for carrying out the disclosure.

INDUSTRIAL APPLICABILITY

The present invention relates to an endoscopic treatment instrument, and is industrially applicable since the endoscopic treatment instrument is applicable to a variety of endoscopic treatment instruments and is reproducible.

The invention claimed is:

1. An endoscopic treatment instrument comprising:
an end-effector, for performing treatment in an endoscopic surgery or an endoscopic treatment;
a connection section, being detachably coupled to an end of the end-effector;
a contamination prevention cover, being coupled to the connection section or the end-effector and surrounding a portion of an outer peripheral surface of the connection section in order to prevent contamination of the connection section; and
a handle unit, controlling an operation of the end-effector and comprising a first handle part being connected to a portion of the end-effector and extending through a coupling part and a second handle part extending through the connection section,
wherein the connection section comprises:
a transmission part being connected to the second handle part; and
a control unit for controlling movement of the connection section by using the transmission part,
wherein a position of the end-effector is controlled by the transmission part,
wherein the end-effector has a membrane disposed between the first handle part and the second handle part.

2. The endoscopic treatment instrument according to claim 1, wherein an inner peripheral surface of a region of the contamination prevention cover is formed to cover an outer peripheral surface of a region of the end-effector.

3. The endoscopic treatment instrument according to claim 1, wherein the end-effector comprises an operation part and an operation module connecting the operation part and the handle unit so that the operation part mechanically operates by the movement of the handle unit.

4. The endoscopic treatment instrument according to claim 1, wherein the contamination prevention cover is made of rubber or synthetic resin.

5. The endoscopic treatment instrument according to claim 4, wherein the handle unit further comprises a first attachment part and a second attachment part that are detachably coupled to each other with the membrane interposed therebetween.

6. The endoscopic treatment instrument according to claim 1, further comprising a contamination prevention cover mounting unit being coupled to an end of the contamination prevention cover, wherein the contamination prevention cover mounting unit comprises:
a main body having a first through-hole formed longitudinally in the main body such that the connection section can be inserted; and
a fluid injection part having a second through-hole formed through the main body to be communicated with the first through-hole.

7. The endoscopic treatment instrument according to claim 6, wherein the contamination prevention cover is configured to expand when a fluid is injected into the contamination prevention cover.

8. The endoscopic treatment instrument according to claim 7, further comprising a plurality of bands arranged longitudinally on the contamination prevention cover,
wherein the plurality of bands are inserted into the contamination prevention cover or attached to an outer peripheral surface of the contamination prevention cover, and
wherein the plurality of bands suppress longitudinal expansion of the contamination prevention cover.

* * * * *